(12) United States Patent
Markovic et al.

(10) Patent No.: US 7,373,676 B2
(45) Date of Patent: May 20, 2008

(54) PATIENT SUPPORT APPARATUS AND METHOD THEREFOR

(75) Inventors: Milan Markovic, Wayne, NJ (US); Nicholas G. Zacharopoulis, New City, NY (US)

(73) Assignee: Aktina Medical Corporation, Congers, NY (US)

( * ) Notice: Subject to any disclaimer, the term of this patent is extended or adjusted under 35 U.S.C. 154(b) by 0 days.

(21) Appl. No.: 11/524,776

(22) Filed: Sep. 21, 2006

(65) Prior Publication Data
US 2008/0072379 A1 Mar. 27, 2008

(51) Int. Cl.
*A61G 13/04* (2006.01)
*A61B 6/04* (2006.01)
(52) U.S. Cl. .............................. 5/601; 5/608; 378/209
(58) Field of Classification Search .................... 5/601, 5/600, 607, 608, 610, 611, 11; 378/209, 378/208, 177, 179, 20
See application file for complete search history.

(56) References Cited

U.S. PATENT DOCUMENTS

| | | | | |
|---|---|---|---|---|
| 4,572,493 | A * | 2/1986 | Hubert | 5/608 |
| 5,398,356 | A * | 3/1995 | Pfleger | 5/608 |
| 6,094,760 | A * | 8/2000 | Nonaka et al. | 5/601 |
| 6,269,499 | B1 * | 8/2001 | Amir | 5/600 |
| 6,416,219 | B1 * | 7/2002 | Pflaum et al. | 378/209 |
| 6,640,363 | B1 * | 11/2003 | Pattee et al. | 5/601 |
| 6,895,617 | B2 | 5/2005 | Zacharopoulos | |
| 6,935,780 | B2 * | 8/2005 | Barde et al. | 378/209 |
| 6,941,599 | B2 | 9/2005 | Zacharopoulos | |
| 7,181,792 | B2 * | 2/2007 | Nakamura et al. | 5/601 |
| 2005/0028280 | A1 * | 2/2005 | Nakamura et al. | 5/601 |

OTHER PUBLICATIONS

Internet site for Medical Intelligence gmbh.

* cited by examiner

*Primary Examiner*—Robert G. Santos
(74) *Attorney, Agent, or Firm*—Jones Day

(57) ABSTRACT

A rotatably adjustable patient support apparatus including a lower base assembly for mounting to a pedestal and an upper base assembly for mounting to a patient couch. The upper and lower base assemblies are connected by three spaced apart connectors, each of which includes two parts joined by a ball joint swivel bearing to enable pivoting of the connector parts about each of two horizontally disposed axes where the axes are perpendicular to one another. One of the connectors is stationary and the other two are mounted to move longitudinally along the base assemblies on guide rails. The guide rails of the upper base assembly are mounted to ramps such that predetermined movement of the two movable connectors cause the upper base assembly to pitch or roll, or to pitch and roll simultaneously. Movement of the two movable connectors is by acme screw and nut sets. A bearing and another acme screw and nut set are mounted to the upper base assembly and together with a pin and slot connector enable a patient couch mounted to the upper base assembly to rotate about a vertical axis independently or simultaneously with the upper base assembly pitching and rolling.

20 Claims, 14 Drawing Sheets

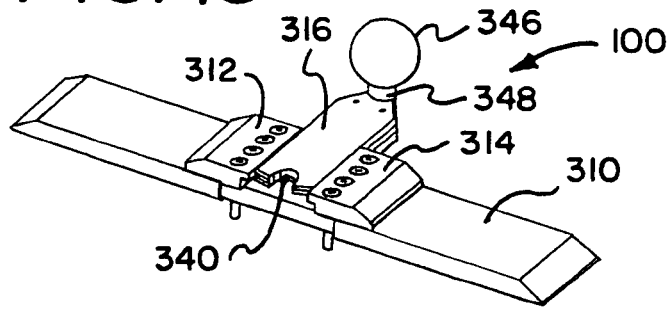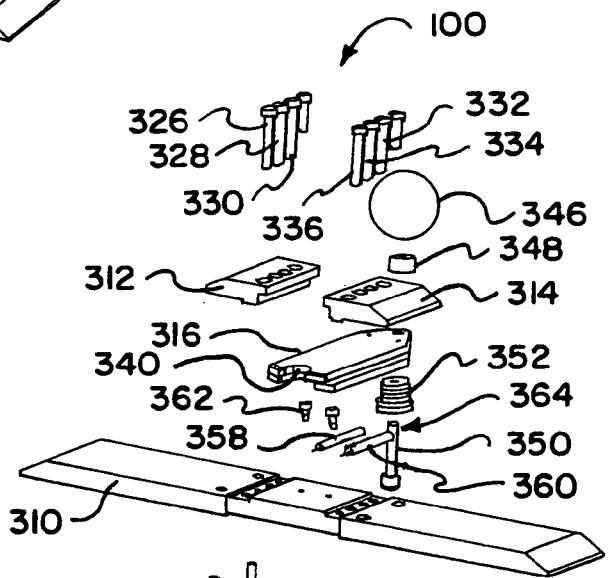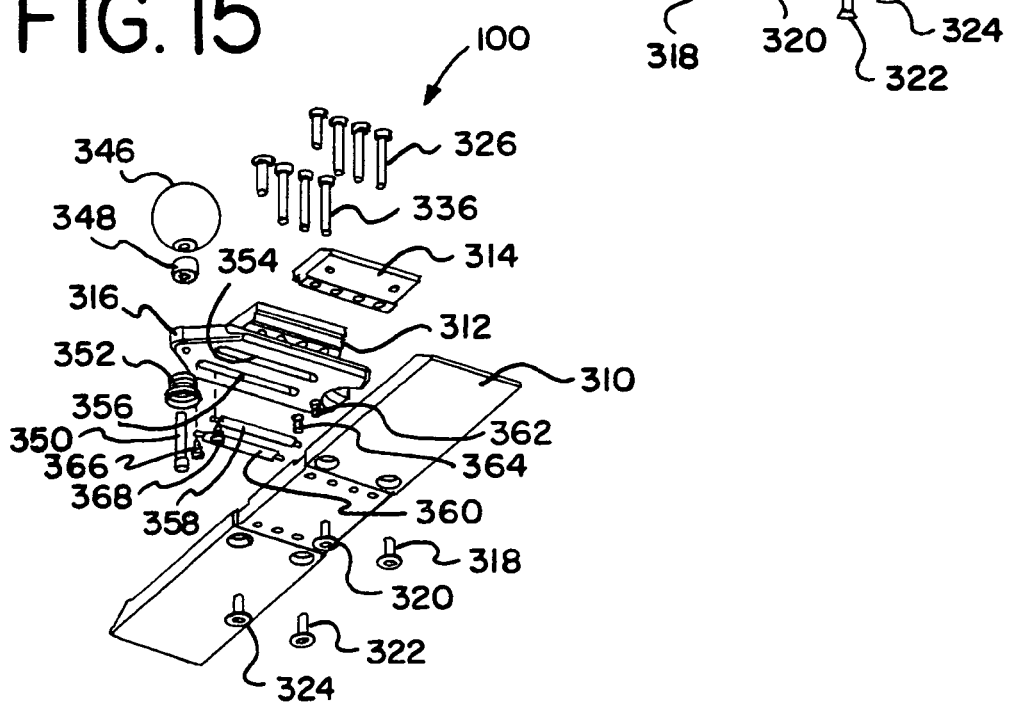

PATENT SUPPORT APPARATUS AND METHOD THEREFOR

CROSS REFERENCE TO PRIORITY APPLICATIONS

Not applicable.

STATEMENT REGARDING FEDERALLY SPONSORED RESEARCH

Not applicable.

BACKGROUND OF THE INVENTION

1. Field of the Invention

The present invention relates to a patient support apparatus, and more particularly, to an improved rotatably adjustable patient support apparatus and method therefor for use, especially, in the field of radiation oncology, the apparatus being capable of rotating about first and second mutually perpendicular horizontal axes and also rotating about a vertical axis.

2. Description of the Related Art

Patient support systems are known, such as those disclosed in U.S. Pat. Nos. 6,941,599 and 6,895,617. The support systems disclosed are capable of moving a patient in three dimensions, often referred to as the x, y and z directions. This terminology will be defined and explained below. As explained in the cited patents, such adjustable patient support systems are useful in radiotherapy. Another support system is disclosed in an Internet site having the address of "Medical-Intelligence.com," and branded as HEXAPOD ROBOTIC TREATMENT COUCH. The HEXAPOD system illustrates a patient support system having six degrees of freedom, defined as linear movements in the x, y and z directions and also rotational movements called pitch, roll and yaw. These rotational movements are about the x, y and z-axes.

The HEXAPOD system includes lower and upper panels or bases which are connected by several links that are pivotally mounted to both the lower and upper panels. By selectively rotating the links, the upper panel may be pivoted and tilted. A drawback to this system, however, is that it is bulky, necessitating too much vertical space between the panels. The extended profile results in difficulty for a patient in mounting the equipment of the system.

BRIEF SUMMARY OF THE INVENTION

The patent support system of the present invention is an improvement on the existing systems described. What is described here is a movable patient support apparatus comprising a first base having a longitudinally extending guide element, the guide element extending along a ramp, a second base spaced from the first base and having a longitudinally extending guide element, a movable connector mounted to move along the guide elements of the first and the second bases, the connector helping support the first base and having first and second parts joined to enable movement about first and second horizontal axes, the first and second axes being perpendicular to each other, a first motion inducing structure connected to the movable connector to enable movement of the movable connector along the longitudinally extending guide elements of the first and the second bases, a stationary connector mounted to the first and the second bases and spaced from the movable connector, the stationary connector helping support the first base and having first and second parts joined to enable movement about the first and the second horizontal axes, and a second motion inducing structure mounted to the first base to enable rotation of a couch supported by the first base about a vertical axis. The invention also includes a method for adjustably rotating the apparatus about three mutually perpendicular axes comprising the steps of connecting the first base to the second base using first, second and third connectors, the connectors enabling rotation about the first and second horizontal axes, mounting a first part of the second connector to the second base to enable linear movement of the first part of the second connector in the direction of the second horizontal axis, mounting the first part of the third connector to the second base to enable linear movement of the first part of the third connector in the direction of the second horizontal axis, mounting a second part of the second connector to a ramp connected to the first base, mounting a second part of the third connector to a ramp connected to the first base, moving the first part of the second connector along the second base, independently moving the first part of the third connector along the second base, and mounting structure on the first base to connect to a patient couch and to enable rotation of the patient couch about the vertical axis.

A complete understanding of the present invention, along with objects, advantages, and features thereof, will be gained from a consideration of the present specification which provides a written description of the invention, and of the manner and process of making and using the invention, set forth in such full, clear, concise and exact terms as to enable any person skilled in the art to which it pertains, or with which it is most nearly connected, to make and use the same in compliance with Title 35, U.S.C. §112 (first paragraph). Furthermore, the following description of the preferred embodiment of the invention read in conjunction with the accompanying drawing provided herein represents an example of the invention in compliance with Title 35, U.S.C. § 112 (first paragraph), but the invention itself is defined in the Claims section attached hereto.

BRIEF DESCRIPTION OF THE SEVERAL VIEWS OF THE DRAWING

FIG. 13 is an isometric view of a portion of a pin and slot connector of the rotatably adjustable support apparatus.

FIG. 14 is a downward looking exploded isometric view of the connector of FIG. 13.

FIG. 15 is an upward looking exploded isometric view of the connector of FIG. 13.

DETAILED DESCRIPTION OF PREFERRED EMBODIMENTS OF THE INVENTION

Figure 1:
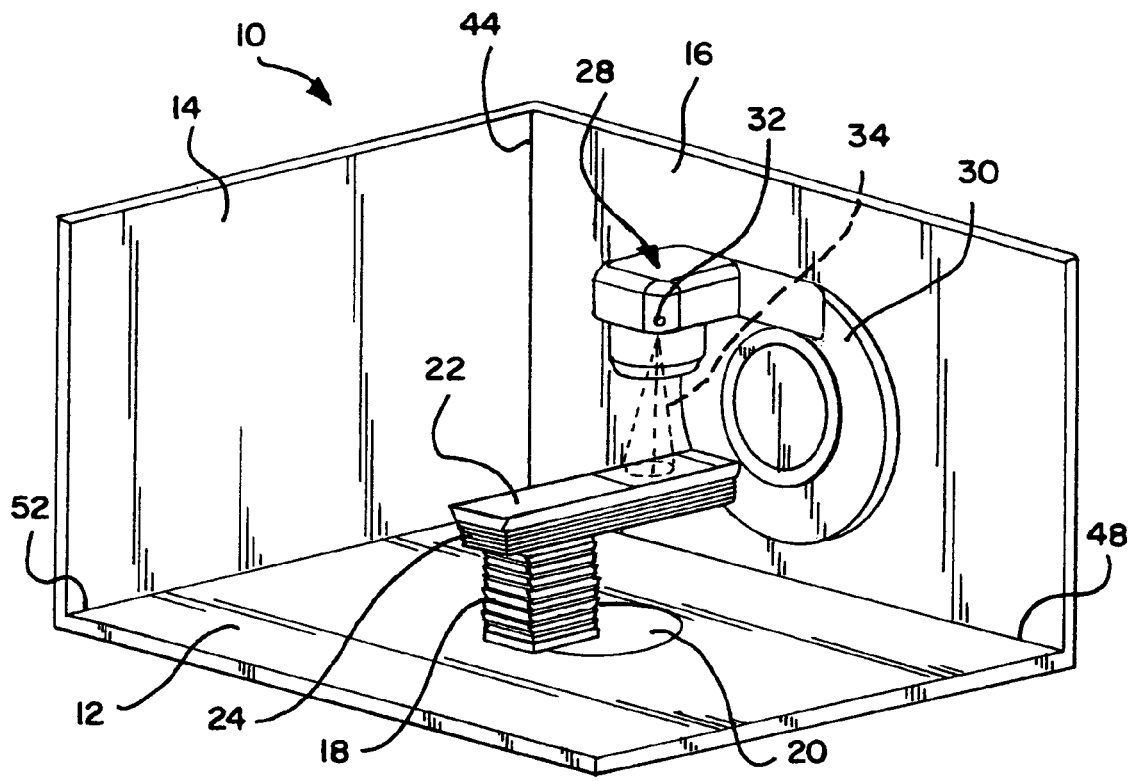
FIG. 1 is a diagrammatic isometric view of a portion of a treatment room with a rotationally adjustable patient support apparatus and a radiation source.

While the present invention is open to various modifications and alternative constructions, the preferred embodiments illustrating the best mode contemplated by the inventor of carrying out his invention are shown in the various figures of the drawing and will be described herein in detail, pursuant to Title 35 U.S.C. §112 (first paragraph). It is noted, however, that there is no intention to limit the invention to the particular embodiments which are disclosed herein. To the contrary, the intention is to cover and claim all modifications, equivalent structures and methods, and alternative constructions falling within the spirit and scope of the invention as expressed in the appended Claims section attached hereto, pursuant to Title 35 U.S.C. §112 (second paragraph).

The patient support apparatus disclosed herein has been conceived and structured for use in the radiation oncology field. A typical location for the support apparatus is a radiotherapy treatment room as shown diagrammatically in FIG. 1. The treatment room portion 10 includes a floor 12 and two walls 14, 16. The remaining building structure as well as unrelated equipment have been removed for purposes of clarity. A vertically extending pedestal 18 is mounted to a rotatable floor panel 20. Mounted to the pedestal is a patient support table or treatment couch 22 upon which a patient is placed during image guided radiation therapy.

Located between the pedestal 18 and the couch 22 is a rotatably adjustable patient support apparatus 24 which will be the focus of this disclosure. The treatment room also includes an accelerator treatment head 28 mounted on a rotatable wall panel 30. The treatment head may also be rotatable and may be movable linearly toward and away from the wall 16. Within the treatment head is a radiation source 32 for transmitting radiation within the field generally depicted by the dotted lines 34.

Figure 2:
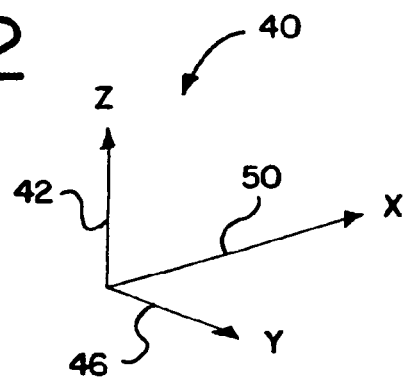
FIG. 2 is an x, y and z coordinate system.

For reference purposes, there is shown in FIG. 2, an x, y, z, three-dimensional coordinate system 40 whose coordinates are mutually perpendicular. The z-coordinate 42 represents a vertical axis and direction which is disposed parallel to an intersection line 44, FIG. 1, of the walls 14, 16. The y-coordinate 46 represents a first horizontal axis and direction perpendicular to the z-axis and is parallel to the intersection line 48 of the wall 16 and the floor 12 and extends laterally across the couch 22. The x-coordinate 50 represents a second horizontal axis and direction which is disposed perpendicular to each of the other two axes (z and y) and which extends parallel to the longitudinal axis of the couch 22. The x-axis is parallel to an intersection line 52 of the wall 14 and the floor 12. The x, y, z coordinate system 40 will be useful when describing various features of the rotatably adjustable patient support apparatus 24 as will be explained in detail below.

Figure 3:
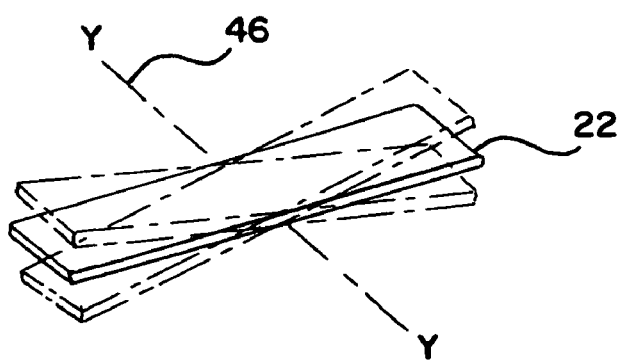
FIG. 3 is a diagrammatic isometric view illustrating a patient support table rotating about the y-axis.
Figure 4:
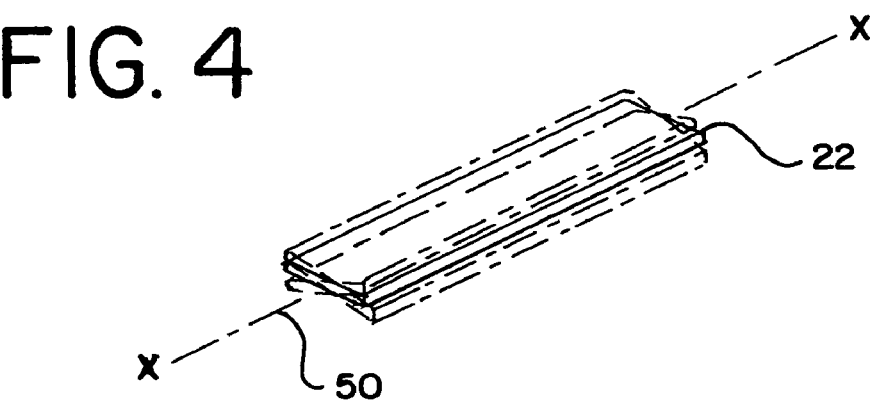
FIG. 4 is a diagrammatic isometric view illustrating a patient support table rotating about the x-axis.
Figure 5:
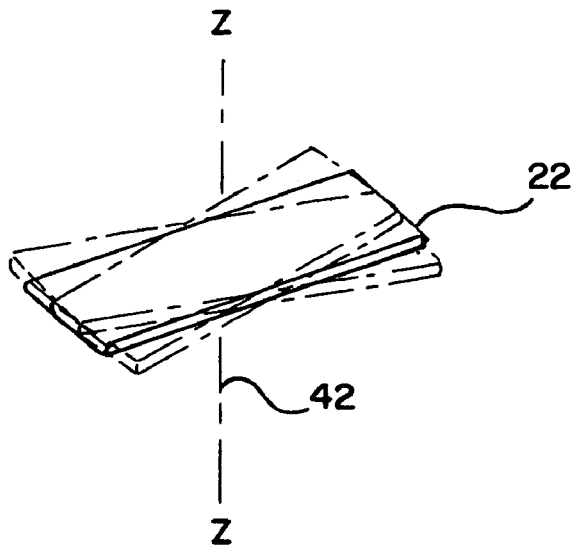
FIG. 5 is a diagrammatic isometric view illustrating a patient support table rotating about the z-axis.

Also, for reference purposes, FIGS. 3-5, illustrate the concepts of "pitch," "roll" and "yaw" and will also be useful when describing the features of the rotatably adjustable patient support apparatus 24. In FIG. 3, the patient support couch 22 is depicted rotating about the y-axis 46, which movement is defined as "pitch." In FIG. 4, the patient support couch 22 is depicted rotating about the x-axis 50 and this movement is termed "roll." Lastly, FIG. 5 illustrates rotation of the couch 22 about the vertical z-axis 42 and this movement is called "yaw."

The two references mentioned above, U.S. Pat. Nos. 6,941,599 and 6,895,617, disclose that the pedestal and couch (or table) are constructed such that the couch may translate or move linearly up and down along the z-axis, left and right along the y-axis and forward and rearward along the x-axis. With the rotatably adjustable patient support apparatus 24 mounted between the pedestal 18 and the patient support table or couch 22 there is an enhancement of couch movement by also allowing the couch to rotate or pivot about each of the x, y, and z axes. In this manner the patient support couch will have six degrees of adjustability to facilitate fine tuning and precise patient positioning for radiation therapy.

Figure 6:
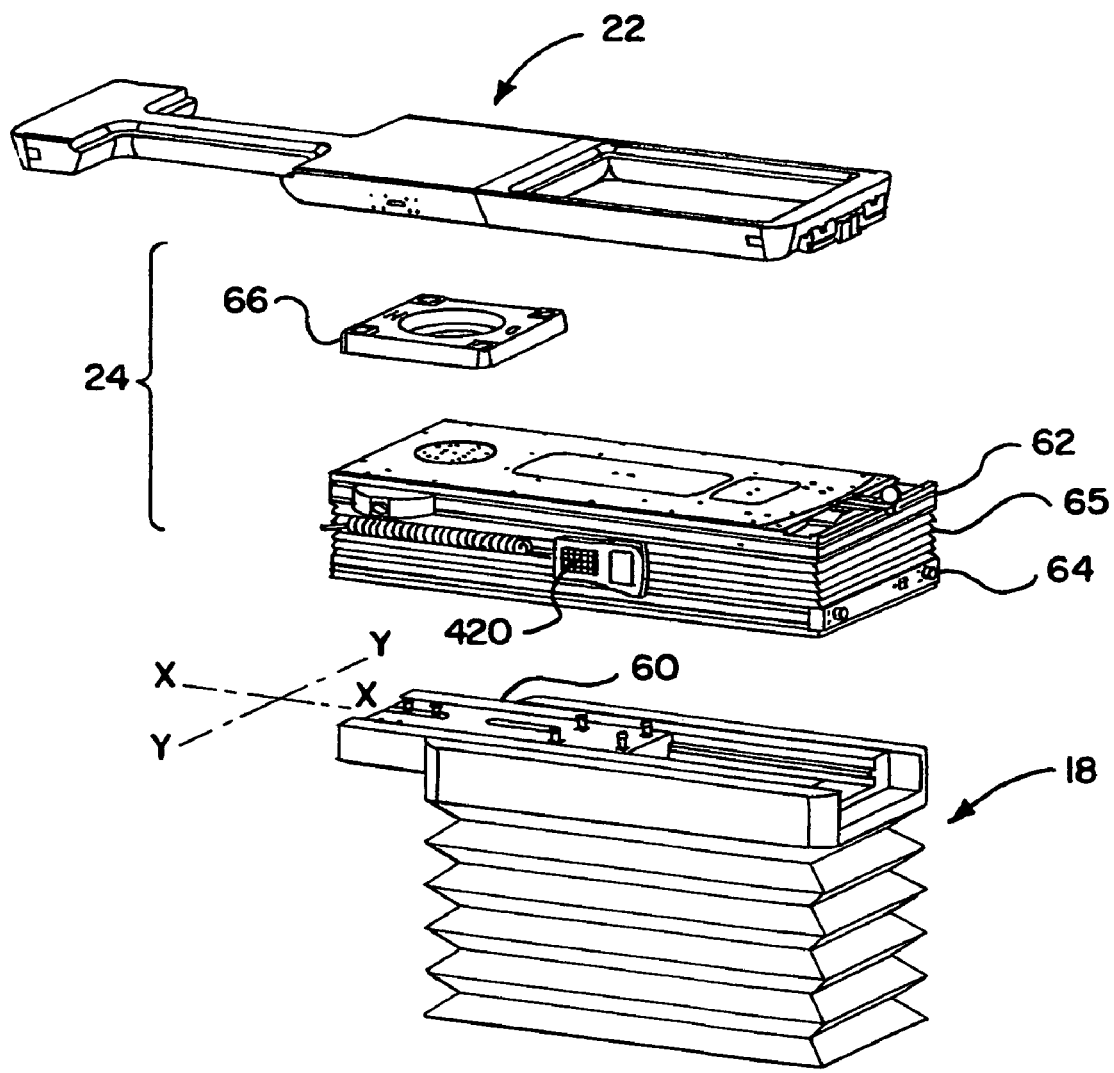
FIG. 6 is an exploded isometric view of the rotationally adjustable patient support apparatus, a pedestal to which the support apparatus is mounted and a treatment couch which is mounted to the support apparatus.

In addition to increasing adjustability to six degrees and providing for precise positioning, the rotatably adjustable patient support apparatus 24 has the advantages of being physically compact and of having a relatively low profile so as to minimize the increased level to which a patient must climb so as to recline on top of the support couch. As shown in FIG. 6, where the pedestal 18, the patient support apparatus 24 and the couch 22 are disposed roughly ninety degrees from that shown in FIG. 1, the pedestal 18 includes a head portion 60 that provides for translation of the patient support apparatus and the couch in the x and y directions as illustrated. The patient support apparatus 24 allows for the fine tuning or minor adjustment of a patient's position prior to treatment. For example, if the object to be treated, a tumor for example, has moved within the patient's body due to weight loss, shift of internal organs, gasses or the like, small adjustments can be made to the position of the couch to compensate. This task is achieved here with a compact, mechanically robust and efficient system that may be original equipment with treatment systems, or it may be retrofitted to existing treatment tables.

Figure 7:
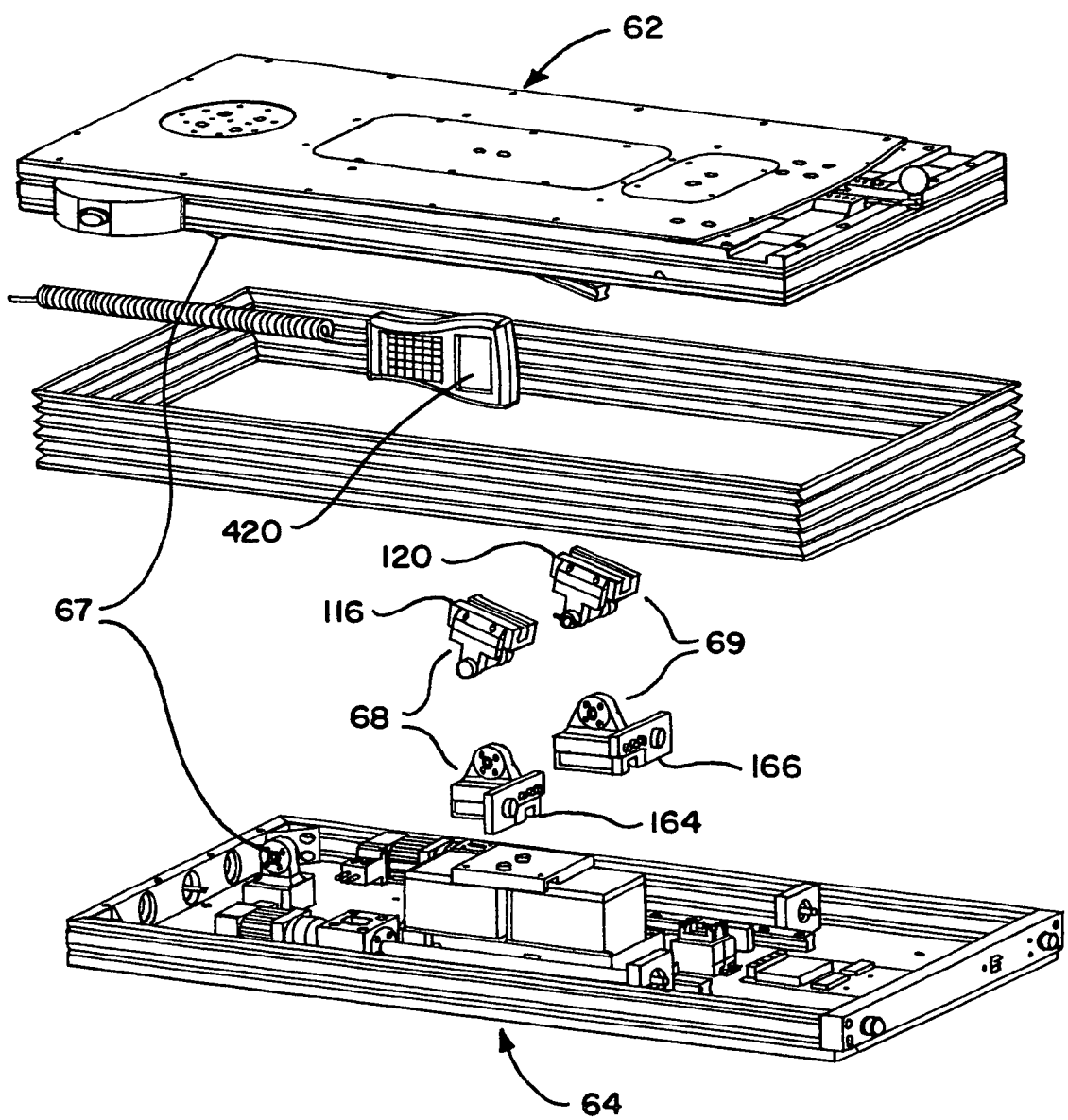
FIG. 7 is an enlarged, exploded isometric view of a portion of the rotatably adjustable support apparatus illustrating upper and lower base assemblies.

In more detail, the rotatably adjustable patient support apparatus 24 includes a first or upper base assembly 62, FIGS. 6 and 7, a second or lower base assembly 64, a bellows shaped cover guard 65 connected between the upper and lower base assemblies and a bearing assembly 66. The upper and lower base assemblies are connected to one another by first, second and third connectors 67, 68, 69. The connectors enable the upper base assembly to rotate or pivot about both of the y and x-axes, and yet be supported along with a patient load above the lower base assembly in the attitude the upper base assembly is placed. The second and third connectors 68, 69 are movable and the first connector 67 is stationary, as will be explained below. The lower base assembly is mounted to the pedestal 18 and the couch 22 may be mounted to the upper base assembly.

Figure 8:
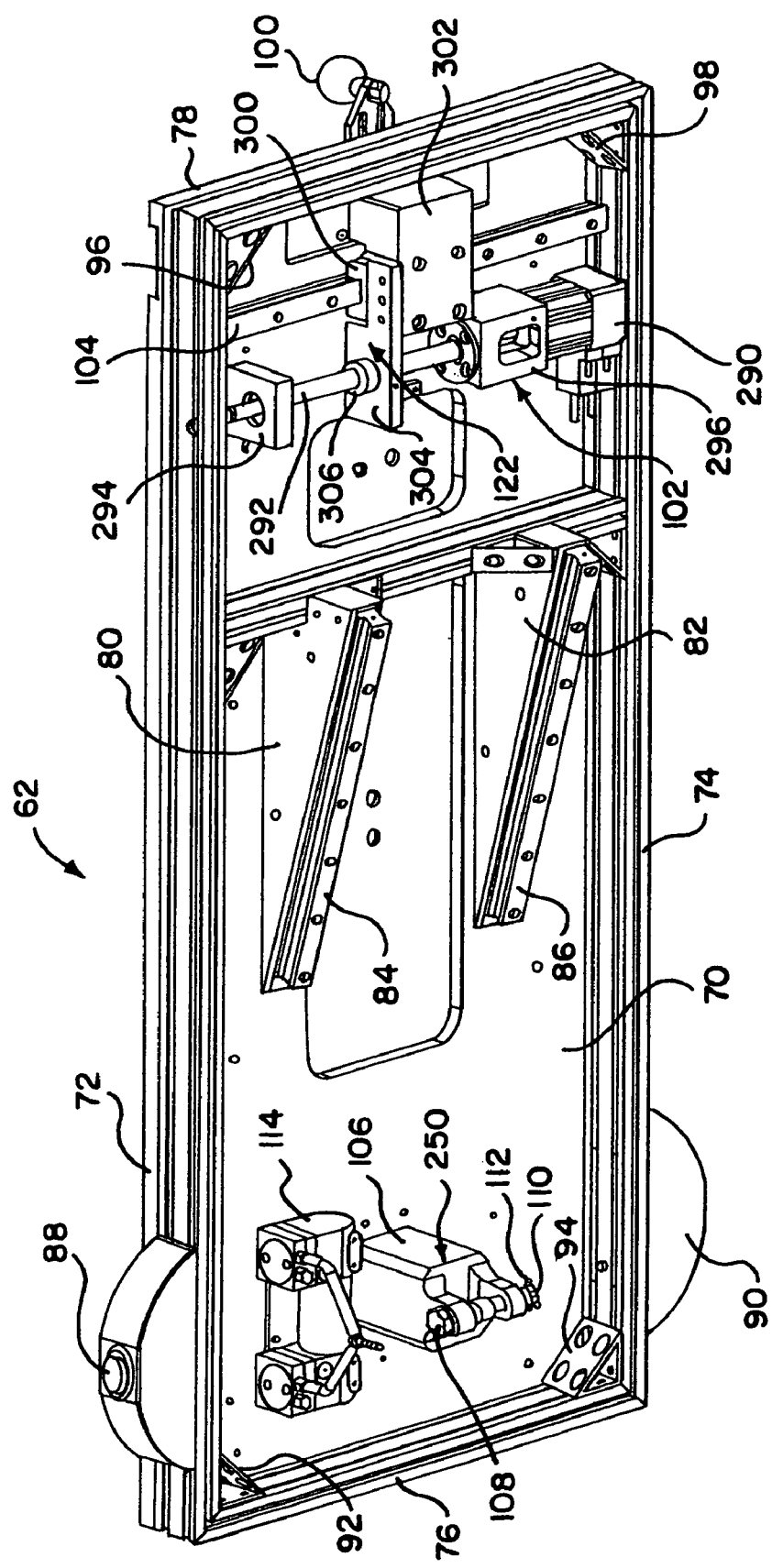
FIG. 8 is an enlarged, upward looking isometric view of the upper base assembly of the rotatably adjustable support apparatus.

The upper base assembly 62 includes an upper mounting panel 70, FIG. 8, two side frames 72, 74 and two end frames 76, 78. Also included are two support wedges or ramps 80, 82, each being generally shaped as a right triangle, mounted to the upper panel 70 along one side of the triangle opposite the larger of the two acute angles, a pair of pathways in the form of upper guide rails 84, 86, one of the pair mounted to each hypotenuse of the triangular support ramps, motion safety switches 88, 90 mounted to the side railings 72, 74, four corner gussets 92, 94, 96, 98 at the intersections of the side and end frames, a fourth connector 100, also referred to as a pin and slot connector, a motion inducing structure to move the fourth connector, the structure in the form of a yaw or lateral actuator assembly 102, a lateral pathway in the form of a guide rail 104, parts of the stationary connector 67 in the form of a shackle bracket 106 mounted to the panel 70, a shoulder screw 108 mounted to the bracket, a castle nut 110 and a cotter pin 112, a vacuum pump 114, parts of the movable connectors 68, 69, in the form of a pair of upper carriages 116, 120, FIG. 7, mounted to be pulled along the upper guide rails 84, 86, and a lateral carriage 122, part of the motion inducing structure to move the pin and slot connector 100, mounted to ride along the lateral guide rail 104.

Figure 9:
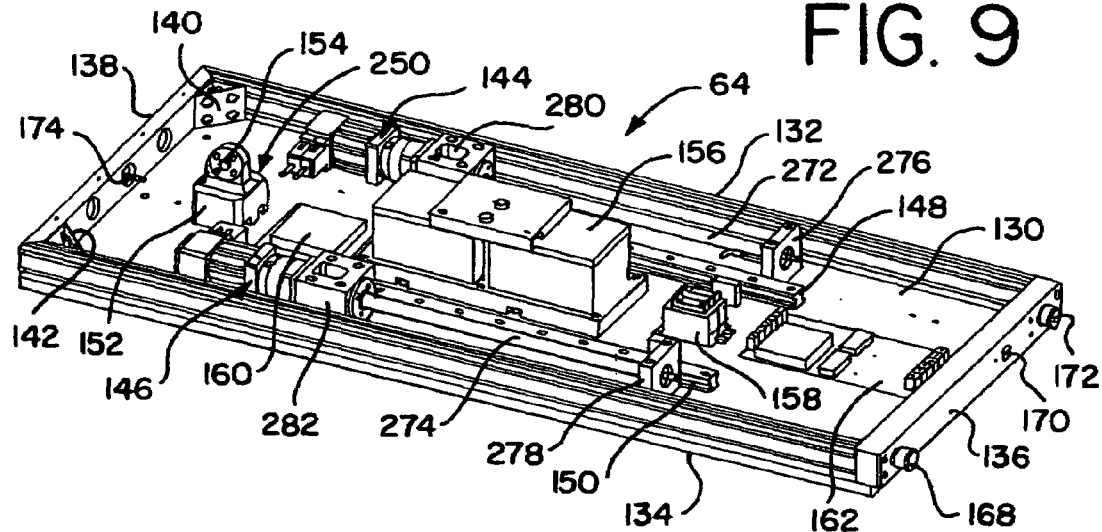
FIG. 9 is a downward looking isometric view of the lower base assembly of the rotatably adjustable support apparatus.
Figure 10:
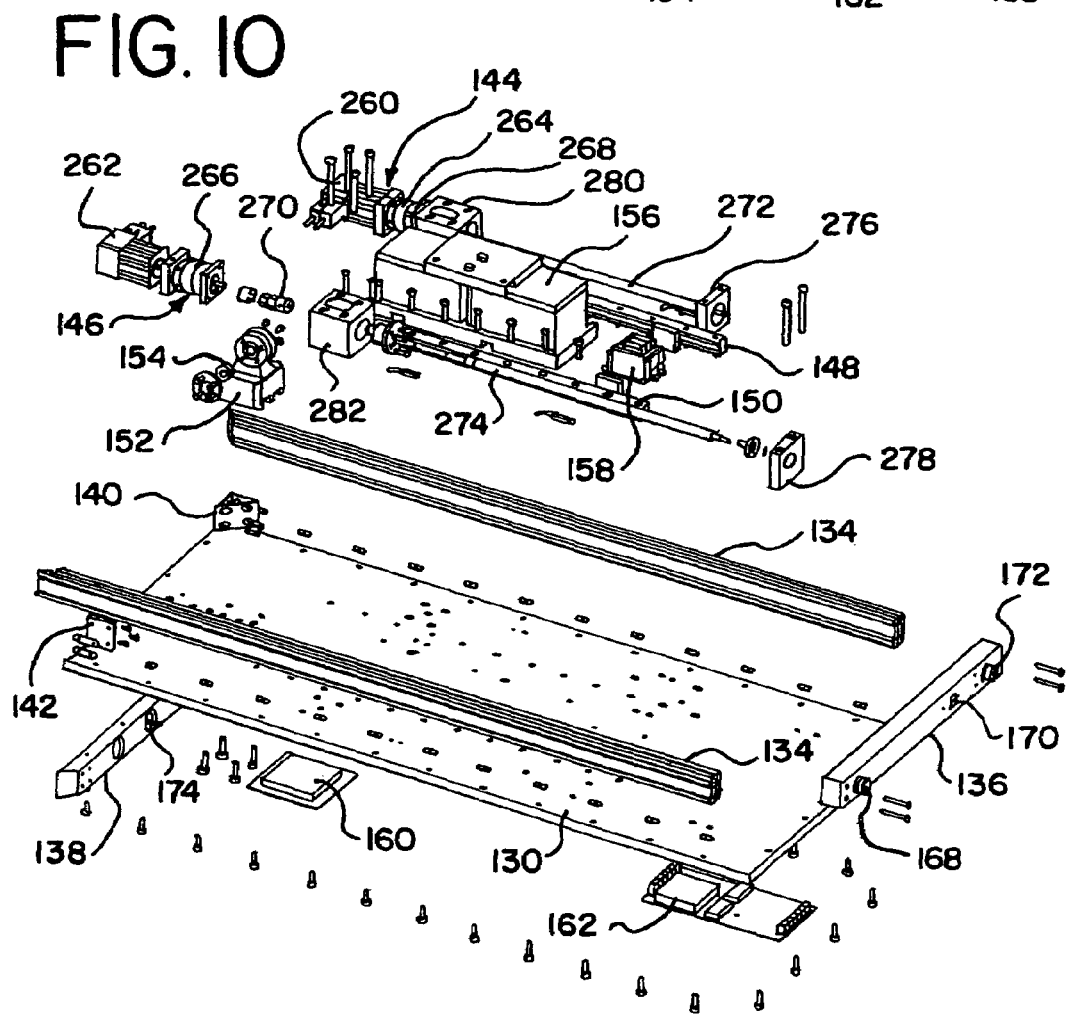
FIG. 10 is an exploded isometric view of the lower base assembly shown in FIG. 9.

The lower base assembly 64 includes a lower mounting panel 130, FIGS. 9 and 10, two side frames 132, 134, a first end frame 136, a second end frame 138, two gussets 140, 142 connecting the side frames and the rear frame, a motion inducing structure to move the second and third connectors 68, 69, the structure being in the form of pitch and roll linear actuator assemblies 144, 146 mounted to the lower panel, a pair of pathways in the form of lower guide rails 148, 150 mounted to the lower panel alongside the actuator assemblies 144, 146, another part of the first connector 67 in the form of a bracket 152 with a ball joint swivel or spherical bearing 154, a battery assembly 156 mounted to the lower panel between the lower guide rails 148, 150, a safety relay 158, a main control module 160, a power distribution board 162 and parts of the second and third connectors 68, 69, the parts being in the form of a pair of lower carriages 164, 166, FIG. 7, mounted to ride along the lower guide rails 148, 150. An e-stop 168, an on/off switch 170 and a battery charging port 172 are mounted to the first end frame 136, and a hand held controller port 174 is formed in the second end frame 138.

Figure 11:
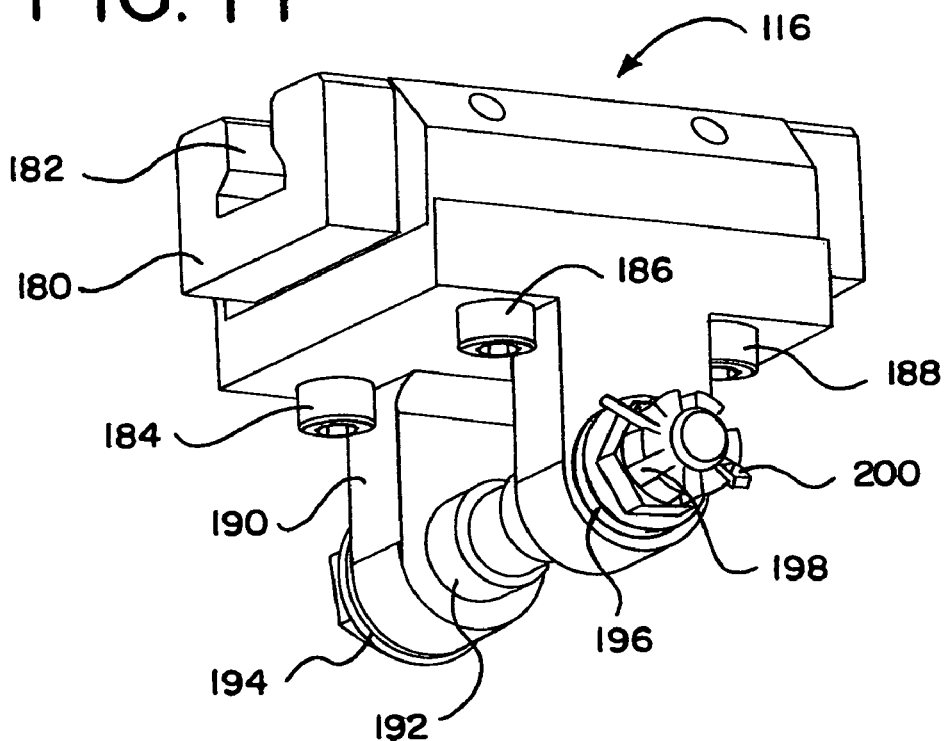
FIG. 11 is an enlarged isometric view of an upper carriage of the rotatably adjustable support apparatus.

Each of the upper carriages 116, 120 includes a runner block 180, FIG. 11, having a generally channel shaped opening 182 for engaging and ridings a respective upper guide rail 84, 86, each of which has a complimentary shape. Connected to the runner block by four screws, of which only three screws 184, 186, 188 are shown, is a yoke shaped carriage block 190 with two openings to receive a bolt or shoulder screw 192. Around the shoulder screw is a washer 194, a bushing 196 and a castle nut 198 along with a cotter pin 200.

Figure 12:
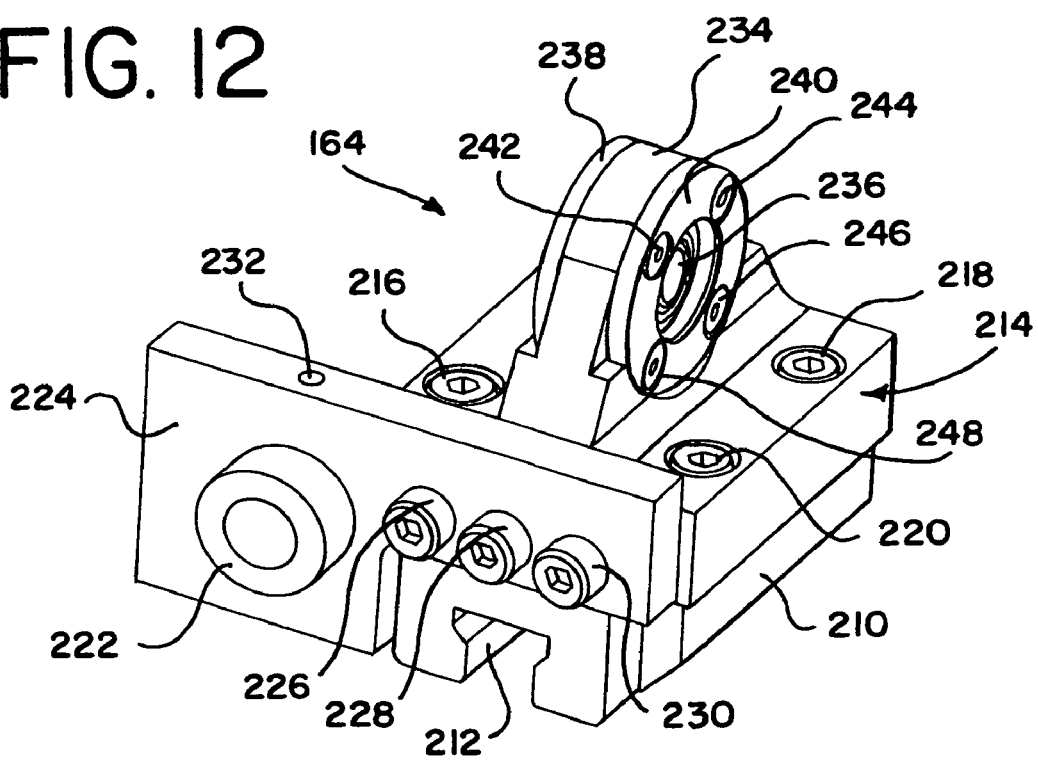
FIG. 12 is an enlarged isometric view of a lower carriage of the rotatably adjustable support apparatus.

Referring now to FIG. 12, there is illustrated in more detail, one of the lower carriages 164, 166. Each lower carriage includes a runner block 210 having a channel shaped opening 212 for engaging and riding one of the lower guide rails 148, 150. The runner block is bolted to a mounting block 214 by four screws of which three screws 216, 218, 220 are shown. An acme nut 222 is mounted to a support plate 224 which in turn is attached by three screws 226, 228, 230 to an end of the mounting block 214. A set screw 232 is used to hold the acme nut 222 in place in the support plate 224. The mounting block 214 includes a flange 234 with an opening for receiving a ball joint swivel bearing 236 held in place by a pair of retainers 238, 240, each retainer being fastened to the flange 234 with four screws 242, 244, 246, 248. Each lower carriage 164, 166 is connected to a corresponding upper carriage 116, 120 by having the swivel bearings 236 receive the bolt or shoulder screw 192 which is retained in place by the castle nut 198 and the cotter pin 200. This structure enables the upper and lower carriages of movable connectors 68, 69 to rotate or pivot relative to one another about both the x and y-axes.

The lower and upper base assemblies are connected together by the two pairs of carriages 116, 120 and 164, 166, which forms the movable connectors 68, 69, and by the first or stationary connector 67 whose parts, the shackle bracket 106, the connector bracket 152, the ball joint swivel bearing 154, along with the shoulder screw 108, the castle nut 110 and the cotter pin 112, have already been identified above. The first stationary connector 67 is constructed in a manner similar to the second and third movable connectors 68, 69. The shoulder screw 108 passes through the shackle bracket 106 and the swivel bearing 154, and is restrained by the castle nut 110 and cotter pin 112. Each of the connectors 67, 68, 69 enables rotational or pivotal motion between the connected parts and they also support the upper base assembly, the couch and the patient. It is noted that other joint structures may be used for the connectors as long as the range of motions and support capability described are available as will be illustrated below.

Each of the pitch and roll actuator assemblies 144, 146, FIGS. 9 and 10 includes a servo motor 260, 262, a gear set 264, 266, a coupling 268, 270 and an acme screw 272, 274. The acme screws 272, 274 are mounted to the lower panel 130 by the bearings in housings 276, 278 and 280, 282. Each acme screw is mounted in the acme nut 222 of the lower carriages 164, 166 such that when the servo motors 260, 262 are activated and the acme screws 272, 274 are rotated, the acme nuts 222 are caused to move linearly in a precise fashion along the acme screws thereby driving the lower carriages 164, 166 riding on the lower guide rails 148, 150. Each of the lower carriages 164, 166 pulls a respective one of the upper carriages 116, 120 along the upper guide rails 84, 86 mounted on the ramps. The upper base assembly 62 responds to movement of the upper carriages by moving in a controlled manner. Movement of the lower carriages is linear in the direction of the x-axis while movement of the upper carriages causes pitching and/or rolling of the upper base assembly because of the shape of the support ramps 80, 82 and the structure of the connectors 67, 68, 69.

The yaw actuator assembly 102, FIG. 8, is structured to enable rotation of the couch 22 or an another variation, a plate to be described below, about the vertical z-axis. The yaw actuator assembly is similar to the pitch and roll actuators 144, 146 and includes a servo motor 290, an acme screw 292 and a pair of bearings 294, 296 for the acme screw, all mounted to the upper panel 70. The lateral guide rail 104 is mounted to the upper panel 70 as well and is parallel to the acme screw 292. Engaging and riding on the lateral guide rail is the lateral carriage 122. The lateral carriage, like each of the lower carriages 164, 166, includes a runner block 300, a mounting block 302 connected to the runner block, a support plate 304 fastened to the mounting block and an acme nut 306 mounted to the support plate. The acme screw extends through the acme nut and when the acme screw is rotated by the servo motor, the lateral carriage 122 is driven linearly along the acme screw 292 and the lateral guide rail 164. The lateral carriage 122 in turn is fastened to the pin and slot connector 100 and causes the pin and slot connector to move laterally as well, enabling the couch to rotate about the z-axis. It is noted that other kinds of actuators may be used as will be set forth below.

Figure 16:
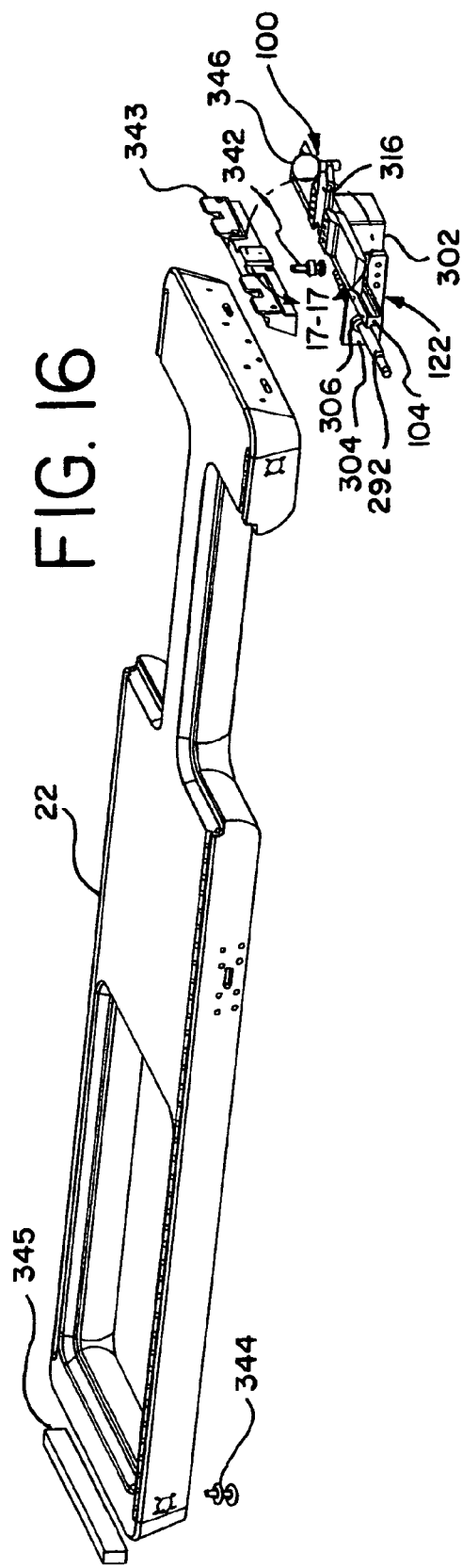
FIG. 16 is an exploded isometric view of the treatment couch, and the pin and slot connector.
Figure 17:
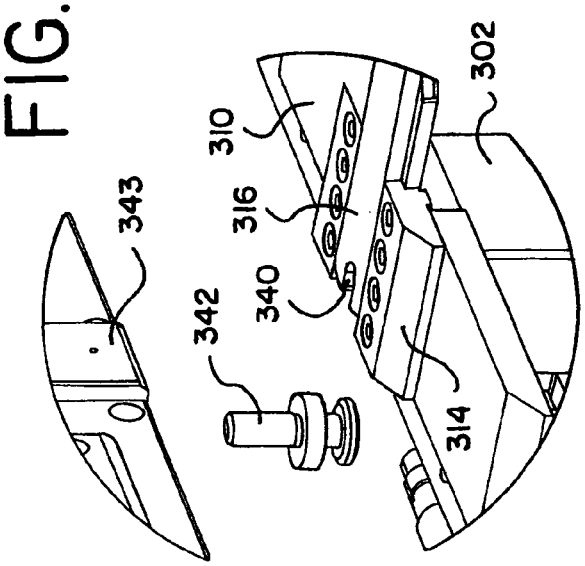
FIG. 17 is an enlarged view taken within the circle 17-17 of FIG. 16.
Figure 32:
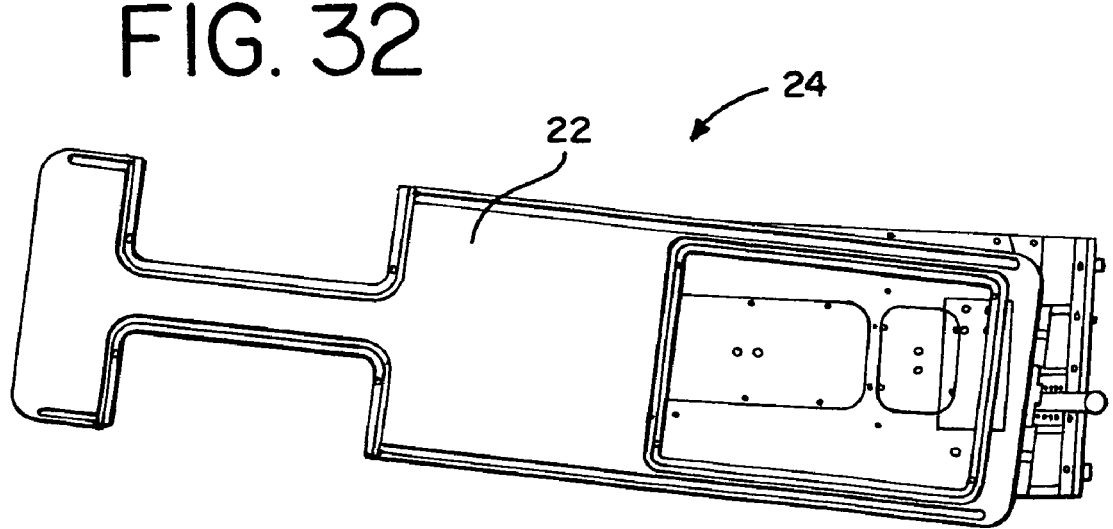
FIG. 32 is a diagrammatic plan view of the couch in yaw.

The pin and slot connector 100 is illustrated in more detail in FIGS. 13-15. The pin and slot connector includes a base plate 310 to which is attached two retainer plates 312, 314 which allow retention of a slidable slot plate 316. Four screws 318, 320, 322, 324 are used to secure the retainer plates to the base plate 310. The base plate 310 is mounted to the mounting block 302, FIG. 8, using six screws 326, 328, 330, 332, 334, 336. The slot plate 316 includes an open slot 340 for engaging a pin 342, FIGS. 16 and 17, connected to an end of the couch, or in an alternate version, a yaw plate. It is noted that a couch may have a pin 342, 344 at each end of the couch, if the couch like that shown in FIG. 16, may be used at either end depending upon the treatment to be provided the patient. Attachment interfaces 343, 345 may be used at each end of the couch for mounting the pins 342, 344. A ball knob 346 is mounted above a spacer 348 and is connected to the slot plate 316 by a screw 350. Beneath the ball knob 346 and the slot plate 316 is a bumper 352 to cushion inward motion of the slot plate. The bottom surfaces of the slot plate 316 includes two grooves 354, 356 into which are placed two coiled springs 358, 360. One end of each of the springs is attached by a screw 362, 364 to the base plate 310 and the other ends of the springs are attached to the slot plate 316 by another pair of screws 366, 368. The springs insure that the slot plate is biased toward the pin to maintain the couch in an engaged condition even when the couch is rotating about the z-axis as shown in FIG. 32. Rotation of the couch with an attached pin occurs when the lateral carriage 122 slides the pin and slot connector 100 laterally or in the y-axis direction. The open slot 340 is sufficiently long to maintain continued engagement with the pin even though the pin moves slightly along the slot and away from the ball knob 346 as the couch rotates. Pulling on the ball knob against the bias of the springs 358, 360, releases the pin 342, 344 and allows the couch to be rotated 180 degrees, from one pin to an oppositely placed pin. Releasing the knob results in the springs returning the slidable slot plate 316 into engagement with the prealigned pin.

Figure 18:
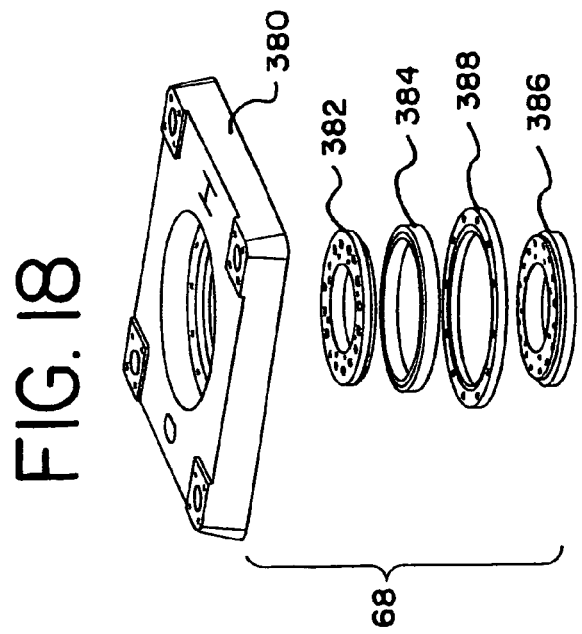
FIG. 18 is an exploded isometric view of a yaw bearing assembly.
Figure 19:
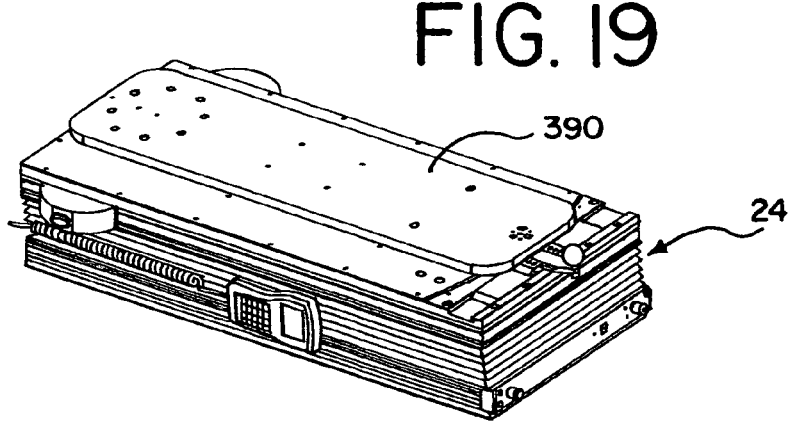
FIG. 19 is an isometric view of a yaw plate attached to the support apparatus.

The bearing assembly 68, FIG. 6, for facilitating rotation about the z-axis comes in two versions. In a version that may be used with an Aktina brand couch shown in FIGS. 16 and 18, the bearing 68 includes a bearing housing 380, a top inner bearing race retainer 382, a crossroller bearing 384, a bottom inner bearing race retainer 386, and an outer bearing race retainer 388. The bearing housing 380 is attached to the couch 22 and the outer bearing race retainer 388 is attached to the upper panel 70. In a version that may be used with other brands of couches, a top plate or panel 390, FIGS. 19 and 20, is provided and the bearing 391 includes a bearing housing 392 attached to the top plate 390 with eight screws 393, 394, 395, 396, 397, 398, 399, 400, a top inner bearing race retainer 401, a bearing 402, a bottom inner bearing race retainer 403 and an outer bearing race retainer 404 which is to be attached to the upper panel 70.

Figure 20:
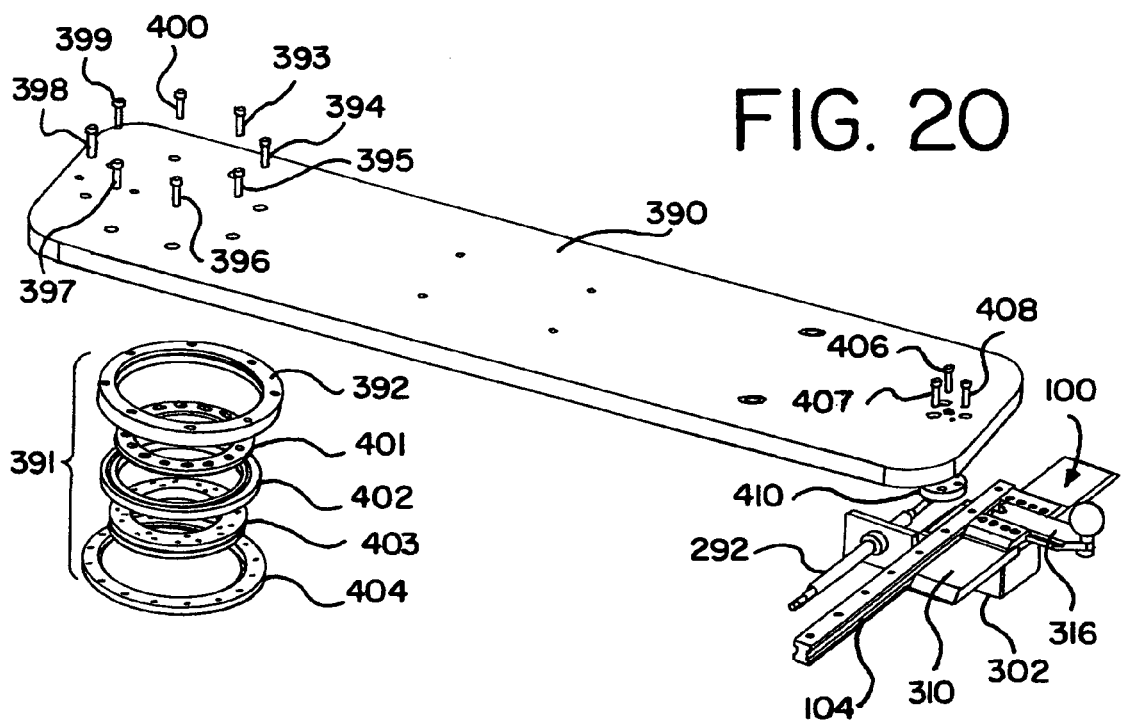
FIG. 20 is an enlarged, exploded isometric view of the yaw plate, a yaw bearing assembly and the pin and slot connector.
Figure 21:
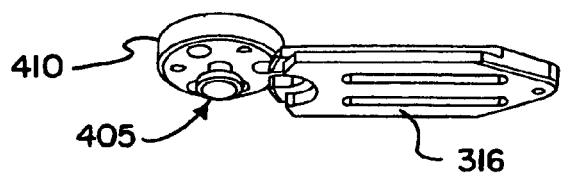
FIG. 21 is an enlarged isometric view of a slot plate and pin of the pin and slot connector.

A pin 405, FIGS. 20 and 21, is attached directly to the top plate 390 using three screws 406, 407, 408 to engage a mounting flange 410 that may be integral with the pin 405. As with the version shown in FIGS. 16 and 17, lateral movement along the y-axis of the lateral carriage 122 causes the slot plate 316 to bear against the pin 405 resulting in rotation of the top plate 390 on the bearing 391 about the z-axis. A couch (not shown) fastened to the top plate will rotate when the top plate rotates.

In operation, the pitch and roll actuators 144, 146 move the movable connectors 68, 69. Because of the joint or hinge between the pairs of carriages of the movable connectors, and because of the stationary connector 67 and the respective locations of the connectors, the upper base assembly 62 is able to rotate about the y and the x-axes. This capability enables the upper base assembly 62 to pitch and roll. When the pin and slot connector 100 is engaged with the lateral actuator 102 and the lateral actuator is activated, the couch is able to also go through a yaw rotation. These rotations may occur independently or they may occur together.

To explain the operation of the adjustable patient support apparatus 24 in even more depth, reference is made to FIGS. 22-32. Pitching and rolling movement is diagrammatically illustrated in FIGS. 22-25 and yaw movement is diagrammatically illustrated in FIGS. 31 and 32. In operation, the lower base assembly 64 is maintained in a level, horizontal position although it is capable of being moved by the pedestal 18 in a linear fashion along the x, y, and z-axes. Because the upper base assembly 62 is connected to the lower base assembly 64, the upper base assembly also moves linearly in the x, y, and z directions in response to lower base assembly movement. Pitching and rolling of the upper base assembly in a precise manner is accomplished by movement of the second and third connectors 68, 69, namely the two pairs of carriages 116, 120 and 164, 166, and by the rotating or pivoting allowed by the structure of the first connector 67. The lower pair of carriages are driven along the lower guide rails 148, 150 by rotation of the lower acme screws 272, 274. Each acme screw is independently operable by energizing a respective lower servo motor 260, 262. Because each of the lower carriages is connected to a respective one of the upper carriages, the upper carriages move in response along the upper guide rails 84, 86 that are attached to the triangular support ramps 80, 82. The lower carriages move linearly and horizontally in a longitudinal direction along the y-axis. Because the upper carriages are mounted to the triangular ramps, they cause the upper panel 70 to rotate or pivot about the x- and y-axes individually or simultaneously.

Figure 22:
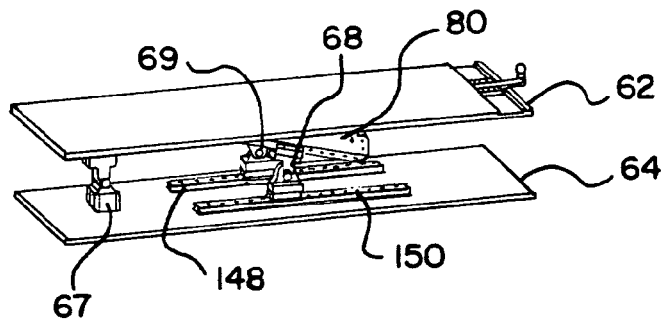
FIG. 22 is a diagrammatic isometric view of the upper and lower base assemblies in parallel alignment.
Figure 23:
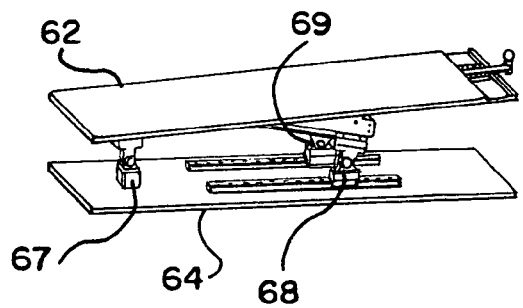
FIG. 23 is a diagrammatic isometric view of the upper base assembly in an upward pitch.

In FIG. 22, the connectors 68, 69 are aligned with one another and are located roughly in the mid-portion of their respective lower guide rails. In this position the upper base assembly 62 is capable of being located in a parallel relationship to the lower base assembly 64 along both the x- and y-axes. As shown in FIG. 23, by moving the connectors 68, 69 along the y-axis while in alignment with one another and away from the stationary connector 67, the upper base assembly 62 is able to rotate about the y-axis, that is pitch, because the two upper carriages 116, 120 move toward the larger of the acute angles of the triangular ramps and push the upper guide rails and thereby the upper base assembly away from the lower base assembly. Rotation is about the center line of the shoulder screw 108 of the stationary connector 67.

Figure 24:
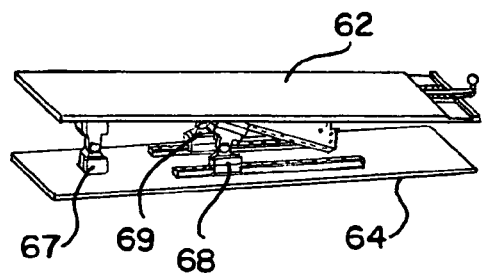
FIG. 24 is a diagrammatic isometric view of the upper base assembly in a downward pitch.

Moving the connectors 68, 69 in the opposite direction, toward the stationary connector 67 causes, as shown in FIG. 24, the upper pair of carriages to move along the upper guide rails toward the smaller of the acute angles of the triangular ramps. This causes the upper base assembly 62 to pivot downwardly rotating about the stationary connector 67.

Figure 25:
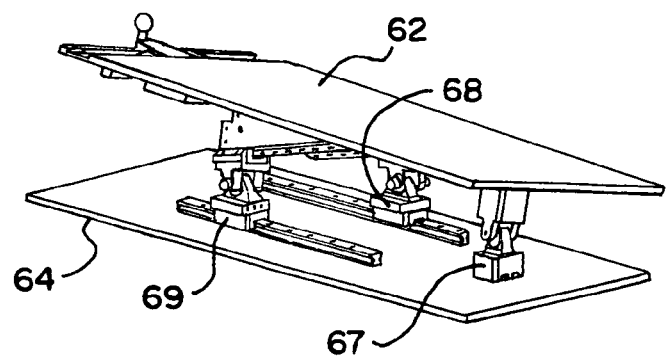
FIG. 25 is a diagrammatic isometric view of the upper base assembly in a roll and pitch.

By moving the two connectors 68, 69 in a non-aligned fashion, that is, moving one of the connectors 68, 69 one way in the z-direction while moving the other of the connectors in the opposite direction as shown in FIG. 25, or by moving the two connectors 68, 69 in the same direction but to different extents, the upper base assembly 62 is caused to roll about the x-axis and the upper base assembly may pitch around the y-axis as well. It can now be appreciated that by moving the two movable connectors 68, 69 in a controlled, predetermined manner, the upper base assembly 62 can pitch or roll, or pitch and roll, within the physical limits of various movement and the configurations of the elements, such as, the geometry and dimensions of the carriages and the rotational limitations of the shoulder screws and ball joint swivel bearings used for the connectors.

The overall dimensions of the patient support apparatus is about 48.8 inches in length, along the x-axis, about 20.0 inches in width, along the y-axis, and about 9.5 inches in height, along the z-axis. This makes for a lower profile and compact package. The triangular ramps may be formed of aluminum and configured generally as right triangles having a short side of about 4.06 inches, a long side of about 15.16 inches and a hypotenuse of about 15.7 inches. The larger of the acute angles is about seventy-five degrees and the smaller of the acute angles or ramp angle is about fifteen degrees. The distance between the guide rails is about 9.5 inches. The distance from the top panel 70 to the center line of the shoulder bolt 108 of the connector 67 is about 4.72 inches and the distance from the upper guide rails 84, 86 to the center lines of the shoulder bolts 192 of the connectors 68, 69 is about 3.07 inches. Each of the lower carriages 164, 166 travels about 14 inches along the lower guide rails to produce desired rotation and the lateral carriage 122 travels about 2.75 inches along the lateral guide rail to produce a 4 degree rotation of the couch.

The mathematical relationship between the positions of the upper panel, the positions of the second and third connectors 68, 69 and the other relevant variables may be understood from the drawings in FIGS. 26-30 and the following equations.

Figure 26:
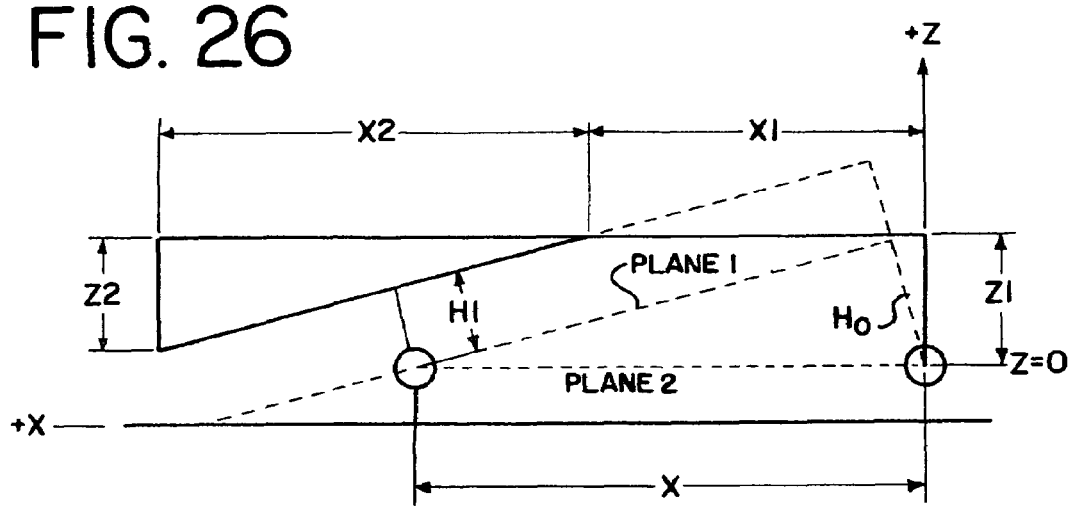
FIGS. 26-30 are graphs and analytical models relating to mathematical equations discussed in the specification.

FIG. 26 is a diagrammatic cross-section of the patient support apparatus where the following dimensions are shown:

$x_1$ $x_2$ $z_1$ $z_2$ and $H_1$.

Also drawn are "Plane1" and "Plane2", and vector $H_0$.

Plane2 is parallel to the lower base assembly and Plane1 is parallel to a plane formed by the upper guide rails 84, 86.

Figure 27:
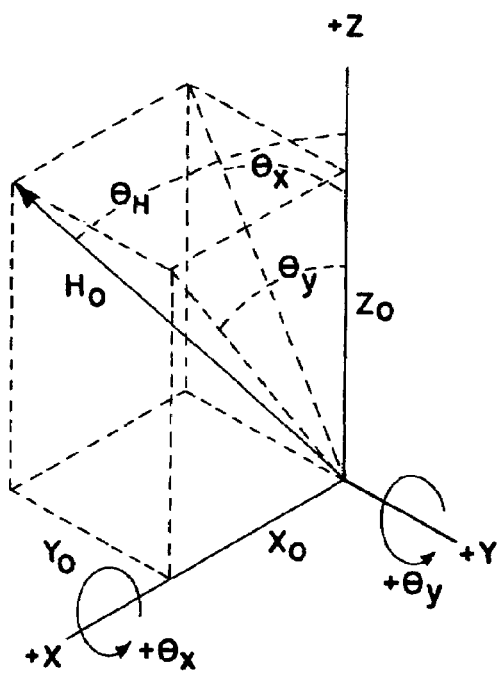

Assuming pitch and roll angles of:

| | |
|---|---|
| $\Theta_x$ | (roll) |
| $\Theta_y$ | (pitch) | the components of $H_0$, where x=0, y=0 and z=0 ($x_0$, $y_0$ and $z_0$) can be described as follows:

$\theta_H = a\tan(\sqrt{\tan^2(\theta_x) \cdot \tan^2(\theta_y)})$ $x_0 = z_0 \cdot \tan(\theta_y)$ $y_0 = z_0 \cdot \tan(\theta_x)$ $z_0 = H_0 \cdot \cos(\theta_H)$, as illustrated in FIG. 27.

Figure 28:
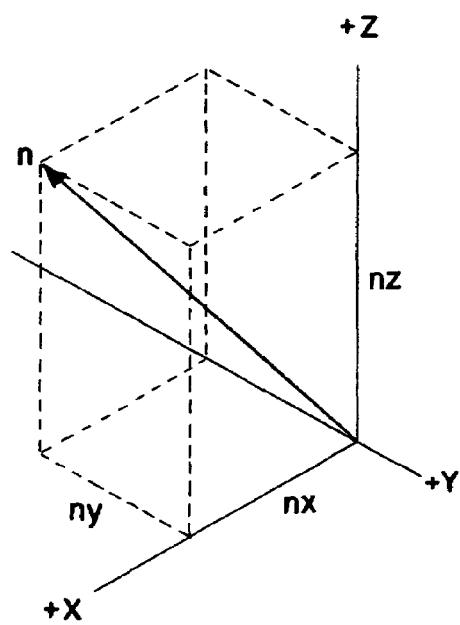

The unit vector of $H_0$ can is defined as following:

$n = \langle n_x, n_y, n_z \rangle$ $n_x = \cos(\theta_H) \cdot \tan(\theta_y)$ $n_y = \cos(\theta_H) \cdot \tan(\theta_x)$ $n_z = \cos(\theta_H)$, as illustrated in FIG. 28.

Figure 29:
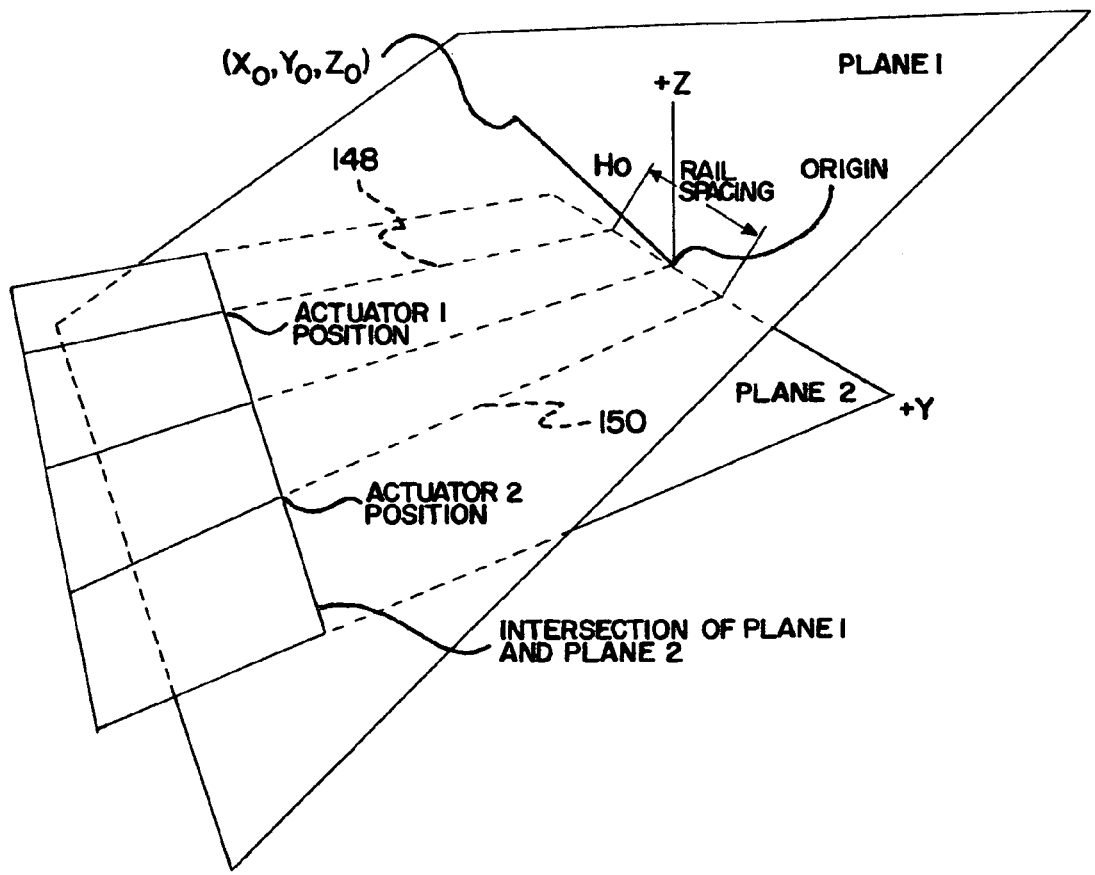

Solve for the x position of the two lower carriages of the second and third connectors 68, 69 by solving for the intersection of Plane1 and Plane2 at the positions as shown in FIG. 29.

Use the unit vector n and the vector $H_0$ to determine the plane passing through point ($x_0$, $y_0$, $z_0$) with normal vector n.

Equation of a Plane 1:

$0 = n_x(x-x_0) + n_y(y-y_0) + n_z(z-z_0)$

With $x_0$, $y_0$, $z_0$, $n_x$, $n_y$, and $n_z$ defined above.
Solve for x to get:

$$x = \frac{n_y}{n_x}(y_0 - y) + \frac{n_z}{n_x}(z_0 - z) + x_0$$

Since the intersection of Plane1 and Plane2 will always be at z=0 and the y position will always be at + and – the (rail spacing)/2, solve for the actuator positions:

$$x_{connector\ 1} = \frac{n_y}{n_x}(y_0 + y_{rail}) + \frac{n_z}{n_x}z_0 + x_0$$

$$x_{connector\ 2} = \frac{n_y}{n_x}(y_0 - y_{rail}) + \frac{n_z}{n_x}z_0 + x_0$$

Where $x_{connector\ 68}$ and $x_{connector\ 69}$ are the connector positions and $y_{rail}$ is ½ the rail spacing.

Figure 30:
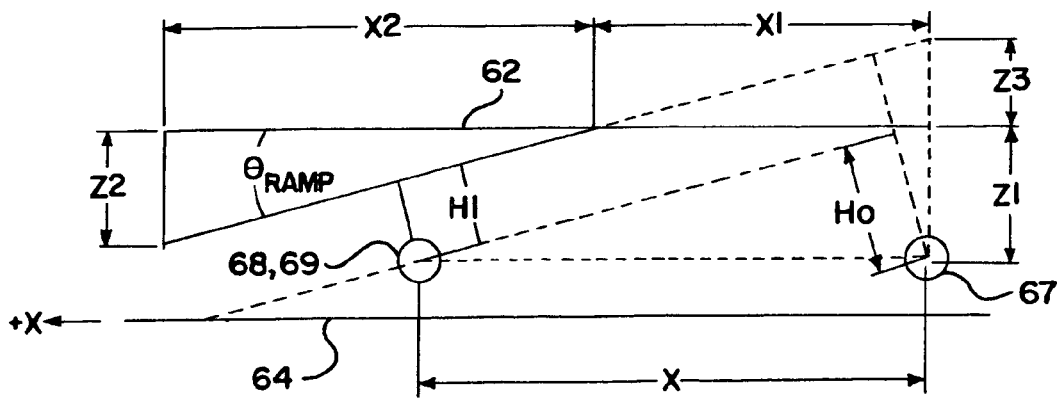

Use the following definitions to determine the length of $H_0$, FIG. 30:

$$z_3 = x_1 \cdot \frac{z_2}{x_2}$$

$$\theta_{ramp} = a\tan\left(\frac{z_2}{x_2}\right)$$

$$H_0 = \cos(\theta_{ramp}) \cdot (z_1 + z_3) - H_1$$

Using the equations with the apparatus disclosed results in the positions of the lower carriages to be about 17.58 inches from the stationary connector 67 when the roll angle $\Theta_x = 0$ and pitch angle $\Theta_y = 0$. For a roll of 2 degrees and no pitch, the carriages are about 16.97 and 18.20 inches from the stationary connector 67. To achieve a roll of about 2 degrees and a pitch of about 3 degrees, the carriages are at about 14.22 inches and about 15.24 inches from the connector 67. For a roll of 2 degrees and a pitch of –3 degrees, the carriages are positioned at about 21.12 inches and 22.67 inches from the stationary connector. Lastly, for a pitch only of −3 degrees (no roll), the carriages are each located about 21.88 inches from the connector 67.

The upper base assembly is minimally capable of pitching, rolling and yawing ±three degrees, although in pure pitch (no roll), the upper base assembly has a maximum movement of 4 degrees, and in pure roll (no pitch), the upper base assembly has a maximum movement of 6 degrees. It is noted that it is difficult to keep a patient from moving relative to the couch due to gravity if pitching or rolling is carried to any greater degrees. Yaw has a maximum movement of about 4 degrees.

Software may be written following the equation above to allow the support apparatus to be controlled by the main control module as explained below.

Figure 31:
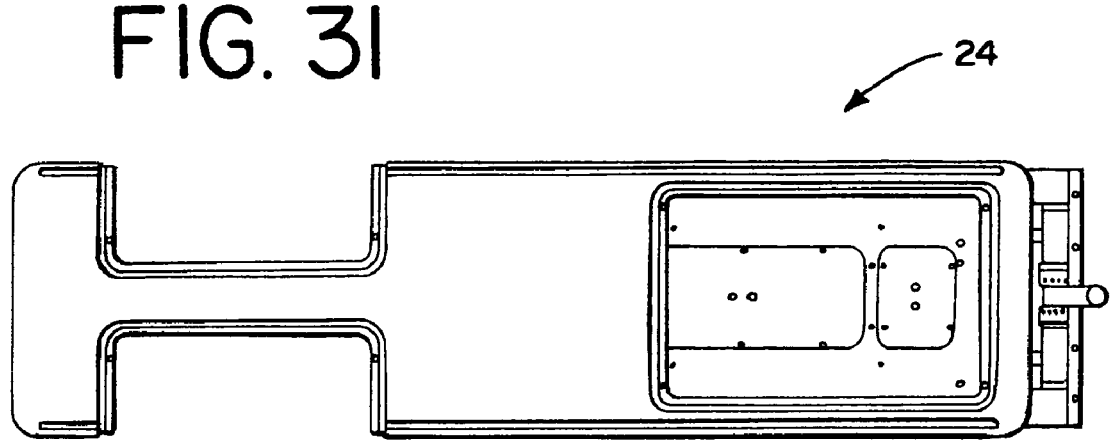
FIG. 31 is a diagrammatic plan view of the couch aligned with the y-axis.

Referring now to FIGS. 31 and 32, the rotatably adjustable patient support apparatus 24 is diagrammatically illustrated undergoing rotation about the z-axis. In FIG. 31, the couch 22 is shown with its longitudinal axis aligned with the y-axis. In FIG. 32, the couch 22 (and the upper base assembly) is shown rotated about the z-axis by about 3.27 degrees.

The patient support apparatus may be controlled by a hand held controller 420, FIGS. 6 and 7, or by a stationery computer, not shown. In either alternative, the main control module 160 is the computer for receiving and computing data, providing necessary commands for controlling movements and providing other output data. The power distribution board 162 provides regulated power to all points of use.

It may be appreciated that the patient support apparatus is easy to operate, has smooth movements, and is relatively simply and inexpensively constructed with many off-the-shelf components.

Another feature of the patient support apparatus is that a power source for the apparatus, the battery assembly 156, FIGS. 9 and 10, is mounted to the lower panel 130. Hence, the patient support apparatus 24 is self contained and may be retrofitted to existing couches without expensive electrical rewiring and without the need for FDA approval.

Yet another feature of the patient support apparatus is the mounting of the vacuum pump 114, FIG. 8, to the upper panel 70. Typically, a couch includes a vacuum cushion (not shown) on the top surface of the couch. The vacuum cushion partially forms to a patient's body shape, is evacuated, and thereby immobilizes the patient on the couch to facilitate locating precisely the region of the body to receive radiation. The vacuum pump helps to evacuate the cushion. Typically, a vacuum pump is in a separate unit that is wheeled into position as needed but otherwise clutters a treatment room. Incorporating the vacuum pump with the patient support apparatus obviates treatment room clutter and unnecessary handling and enhances operator convenience. Both time and effort are saved.

The patient support apparatus also includes the safety switches 88, 90, FIG. 8. These may be "dead-man" switches that must be depressed at all times of operation of the apparatus. Letting go of a switch causes the apparatus to shut off. The battery assembly, the vacuum pump and the safety switches are all well known to those skilled in engineering.

The above specification describes in detail preferred embodiments of the present invention. Other examples, embodiments, modifications and variations will, under both the literal claim language and the doctrine of equivalents, come within the scope of the invention defined by the appended claims. For example, changing the structure of the connectors 67, 68, 69, or the ramps, or the guide rails or the actuators are considered equivalent structures and will also come within the literal language of the claims. For example, using a ball screw and nut, other types of lead screws, timing belt actuators, hydraulic and pneumatic cylinders, linear motors, gear drives, drive belts and chain drives or the like, instead of an acme screw and nut set, is considered equivalent structures and any of these would literally infringe many of the claims. Likewise, changing the shape of the ramps, or constructing them as a framework, or both, are also considered to be a literal infringement. Another example of a variation is to mount the carriages to wheels, skids, tracks, or the like and have the carriages move along pathways on the upper and lower base assemblies instead of using rails. By way of additional examples, using a living hinge, a ball and socket or a universal joint are also considered alternative but infringing structure. Still other alternatives will also be equivalent as will many new technologies. There is no desire or intention here to limit in any way the application of the doctrine of equivalents nor to limit or restrict the scope of the invention.

The invention claimed is:

1. A rotatably adjustable patent support apparatus comprising:
   a first base having a longitudinally extending guide element, the guide element extending along a ramp;
   a second base spaced from the first base and having a longitudinally extending guide element;
   a movable connector mounted to move along the guide elements of the first and the second bases, the connector helping support the first base and having first and second parts joined to enable movement about first and second horizontal axes, the first and second axes being perpendicular to each other;
   a first motion inducing structure connected to the movable connector to enable movement of the movable connector along the longitudinally extending guide elements of the first and the second bases;
   a stationary connector mounted to the first and second bases and spaced from the movable connector, the stationary connector helping support the first base and having first and second parts joined to enable movement about the first and second horizontal axes; and
   a second motion inducing structure mounted to the first base to enable rotation of a couch mounted to the first base to rotate about a vertical axis.

2. The apparatus as claimed in claim 1 wherein:
   the movable connector includes a ball joint swivel bearing.

3. The apparatus as claimed in claim 1 wherein:
   the stationary connector includes a ball joint swivel bearing.

4. The apparatus as claimed in claim 1 wherein:
   the first motion inducing structure connected to the movable connector to enable movement includes a motor, an acme screw and an acme nut.

5. The apparatus as claimed in claim 1 wherein:
   the second motion inducing structure mounted to the first base to enable rotation of the first base includes a second movable connector and structure to move the second movable connector.

6. The apparatus as claimed in claim 5 wherein:
   the structure to move the second movable connector includes a carriage, an acme screw and an acme nut.

7. The apparatus as claimed in claim 2 wherein:
   the stationary connector includes a ball joint swivel bearing;
   the structure connected to the movable connector to enable movement includes a motor, an acme screw and an acme nut; and the structure mounted to the first base to enable rotation of the first base includes a second movable connector and structure to move the second movable connector.

8. The apparatus as claimed in claim 1 wherein:
the first base includes two longitudinally extending guide elements, each of the guide elements being mounted to a ramp;
the second base includes two longitudinally extending guide elements;
the movable connector is mounted to one guide element of the first base and one guide element of the second base;
the structure mounted to the first base to enable rotation of a couch includes a second movable connector and structure to move the second movable connector; and including
a third movable connector, the third movable connector have first and second parts joined to enable movement about the first and the second horizontal axes, the third movable connector being mounted to the other guide element of the first base and to the other guide element of the second base.

9. The apparatus as claimed in claim 8 wherein:
the structure connected to the first mentioned movable connector includes a first acme screw and a first acme nut;
the structure connected to the second movable connector to move the second movable connector includes a second acme screw and a second acme nut; and including
structure connected to the third movable connector to enable movement of the third movable connector along the other guide elements, the structure including a third acme screw and a third acme nut.

10. The apparatus as claimed in claim 9 wherein:
the structure mounted to the first base to enable rotation of a couch mounted to the first base includes a bearing.

11. The apparatus as claimed in claim 10 wherein:
the first mentioned and third movable connectors each includes a ball joint swivel bearing.

12. The apparatus as claimed in claim 11 including:
a battery mounted to the second base; and
a vacuum pump mounted to the first base.

13. The apparatus as claimed in claim 1 including:
a battery mounted to the second base.

14. The apparatus as claimed in claim 1 including:
a vacuum pump mounted to the first base.

15. A method for adjustably rotating a patient support apparatus about a first horizontal axis, about a second horizontal axis disposed perpendicular to the first horizontal axis and about a vertical axis, the method comprising the steps of:
connecting a first base to a second base with first, second and third connectors, the connectors enabling rotation about the first and the second horizontal axes;
mounting a first part of the second connector to the second base to enable linear movement of the first part of the second connector in the direction of the second horizontal axis;
mounting a first part of the third connector to the second base to enable linear movement of the first part of the third connector in the direction of the second horizontal axis;
mounting a second part of the second connector to a first ramp connected to the first base;
mounting a second part of the third connector to a second ramp connected to the first base;
moving the first part of the second connector along the second base;
independently moving the first part of the third connector along the second base; and
mounting structure on the first base to connect to a patient couch and to enable rotation of the patient couch about the vertical axis.

16. The method as claimed in claim 15 including the step of:
mounting a bearing on the first base to facilitate rotation about the vertical axis.

17. The method as claimed in claim 16 wherein:
each of the first, second and third connectors includes a ball joint swivel bearing.

18. The method as claimed in claim 17 wherein:
the mounting structure comprises an acme screw and nut set and a pin and slot connector, the pin being connected to a couch and the slot being connected to the first base.

19. A rotatably adjustable patient support apparatus comprising:
a first base having two longitudinally extending pathways, each of the pathways extending along a ramp;
a second base spaced from the first base and having two longitudinally extending pathways;
first and second movable connectors mounted to move along the pathways of the first and the second bases, the movable connectors for supporting the first base, each movable connector having first and second parts joined to enable movement about first and second horizontal axes, the first and second horizontal axes being perpendicular to each other;
a first motion inducing structure connected to the first movable connector to enable movement of the first movable connector along the longitudinally extending pathways of the first and the second bases;
a second motion inducing structure connected to the second movable connector to enable movement of the second movable connector along the longitudinally extending pathways of the first and the second bases;
a stationary connector mounted to the first and second bases and spaced from the first and second movable connectors, the stationary connector for supporting the first base and having first and second parts joined to enable movement about the first and second horizontal axes;
a third movable connector mounted to the first base;
a laterally extending pathway connected to the first base;
a third motion inducing structure connected to the third movable connector to enable movement of the third movable connector along the laterally extending pathway; and
a bearing structure mounted to the first base to enable rotation around a vertical axis of a couch mounted to the first base.

20. The apparatus as claimed in claim 19 wherein:
the first and second movable connectors and the stationary connector each includes a ball joint swivel bearing; and
the first, second and third motion inducing structures each includes an acme screw and acme nut.

* * * * *

UNITED STATES PATENT AND TRADEMARK OFFICE
CERTIFICATE OF CORRECTION

PATENT NO. : 7,373,676 B2 Page 1 of 1
APPLICATION NO. : 11/524776
DATED : May 20, 2008
INVENTOR(S) : Markovic et al.

It is certified that error appears in the above-identified patent and that said Letters Patent is hereby corrected as shown below:

In column 12, line 20, claim 1, delete "patent" and insert -- patient --.

In column 14, line 11, claim 16, delete the semicolon ";" and replace with a colon -- : --.

Signed and Sealed this

Twenty-ninth Day of July, 2008

JON W. DUDAS
*Director of the United States Patent and Trademark Office*